(12) United States Patent
Jiang

(10) Patent No.: US 8,094,780 B2
(45) Date of Patent: *Jan. 10, 2012

(54) TWO DIMENSIONAL SMALL ANGLE X-RAY SCATTERING CAMERA

(75) Inventor: Licai Jiang, Rochester Hills, MI (US)

(73) Assignee: Rigaku Innovative Technologies, Inc., Auburn Hills, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/753,989

(22) Filed: Apr. 5, 2010

(65) Prior Publication Data

US 2010/0284516 A1    Nov. 11, 2010

Related U.S. Application Data

(63) Continuation of application No. 11/948,304, filed on Nov. 30, 2007, now Pat. No. 7,734,011, which is a continuation of application No. PCT/US2006/000290, filed on Jan. 4, 2006, which is a continuation of application No. 11/142,862, filed on May 31, 2005, now Pat. No. 7,139,366.

(51) Int. Cl.
  *G01N 23/201* (2006.01)
(52) U.S. Cl. ............................................. 378/86; 378/87
(58) Field of Classification Search ...................... 378/87, 378/84, 86, 88, 89, 90
See application file for complete search history.

(56) References Cited

U.S. PATENT DOCUMENTS

| | | |
|---|---|---|
| 4,749,562 A | 6/1988 | Lane et al. |
| 4,751,722 A | 6/1988 | Harding et al. |
| 4,956,856 A | 9/1990 | Harding |
| 5,016,267 A | 5/1991 | Wilkins |
| 5,028,352 A | 7/1991 | Hietala et al. |
| 5,619,548 A | 4/1997 | Koppel |
| 5,684,857 A | 11/1997 | De Bokx et al. |

(Continued)

FOREIGN PATENT DOCUMENTS

DE       199 55 848 A1     5/2000

(Continued)

OTHER PUBLICATIONS

A Small Angle X-Ray Scattering Study of the Effect of Pressure on the Aggregation of Asphaltene Fractions in Petroleum Fluids under Near-Critical Solvent Conditions, N.F. Carnahan, L. Quintero, D.M. Pfund, J.L. Fulton, R.D. Smith, M. Capel, K. Leontaritis, 1993, American Chemical Society, pp. 2035-2044.

(Continued)

*Primary Examiner* — Hoon Song
(74) *Attorney, Agent, or Firm* — Brinks Hofer Gilson & Lione

(57) ABSTRACT

A two-dimensional x-ray scattering camera includes a source, an optic, a detector, and a pair of collimating blocks. The source emits x-ray beams that are reflected by the optic towards a sample. The detector detects scattering from the sample, the pair of collimating blocks is positioned between the optic and the detector to collimate the beam. A bottom surface of one block is substantially parallel a top surface of the other block, and the blocks are rotatable relative to the beam about a pivot. The system forms a two-dimensional beam that is symmetric about the primary beam axis at the detector position, regardless how the beam is collimated by the collimating blocks. The system therefore eliminates smearing and can be used for anisotropic small angle scattering at high resolution and low $Q_{min}$.

28 Claims, 5 Drawing Sheets

U.S. PATENT DOCUMENTS

| | | | |
|---|---|---|---|
| 6,014,423 | A | 1/2000 | Gutman et al. |
| 6,041,099 | A | 3/2000 | Gutman et al. |
| 6,054,712 | A | 4/2000 | Komardin et al. |
| 6,175,117 | B1 | 1/2001 | Komardin et al. |
| 6,196,715 | B1 | 3/2001 | Nambu et al. |
| 6,330,301 | B1 | 12/2001 | Jiang |
| 6,444,993 | B1 | 9/2002 | Kogan |
| 6,459,761 | B1 | 10/2002 | Grodzins et al. |
| 6,483,891 | B1 * | 11/2002 | Lazarev et al. .................. 378/37 |
| 6,643,354 | B2 * | 11/2003 | Koppel et al. ................... 378/86 |
| 7,139,366 | B1 * | 11/2006 | Jiang ............................... 378/88 |
| 7,734,011 | B2 * | 6/2010 | Jiang ............................... 378/86 |
| 2003/0016783 | A1 | 1/2003 | Grodzins et al. |

FOREIGN PATENT DOCUMENTS

| | | |
|---|---|---|
| EP | 1 477 796 A2 | 11/2004 |
| JP | 9-49811 | 2/1997 |
| JP | 9054050 A | 2/1997 |
| JP | 11-64593 | 3/1999 |
| JP | 2003517603 | 5/2009 |
| WO | WO 2006/130182 A1 | 12/2006 |

OTHER PUBLICATIONS

Construction of a Small-Angle X-Ray Scattering Diffractometer for the Study of Fluctuations in Solutions, Hisashi Hayashi, Kelko Nishidawa and Takao Iijima, Japanese Journal of Applied Physics, vol. 28, No. 8, Aug. 1989, pp. 1501-1503.

Apparatus for simultaneous observation of the electro-optic response and small angle x-ray scattering in liquid crystals; H.F. Gleeson, C. Carboni and A.S. Morse; American Institute of Physics, 1995, pp. 3563-3568.

PIXE setup for liquid sample analysis, J. Kral, J. Voltr, Z. Nejedly; Nuclear Instruments and Methods in Physics Research B 109/110 (1996) pp. 167-169.

Small-Angle X-Ray Scattering Study of Polyelectrolyte Solutions; M. Tomsic, M. Bester Rogac and A. Jamnik; Acta Chism. Slov. 2001, 48, pp. 333-342.

Small Angle X-Ray Scattering; 3.1 Instrumentation. Experimental technique, Slit Collimation, O. Kratkey; and 3.111 Instrumentation. Data Collection in X-ray Small Angle Scattering, H. Leopold, London; New York: Academic Press, 1982, pp. 53-83 and pp. 85-117.

Two approaches for irradiating cells individually: a charged-particle microbeam and a soft X-ray microprobe; M. Folkard, B. Vojnovic, G. Schettino, M. Forsberg, G. Bowey, K. M. Prise, B.D. Michael, A.G. Michette, S.J. Pfauntsch; Nuclear Instruments and Methods in Physics Research B 130 (1997) pp. 270-274.

Characterization of pore distribution in activated carbon fibers by microbeam small angle X-ray scattering; D. Loznano-Castello, E. Raymund- Pinero, D. Cazorla-Amoros, A. Linares-Solano, M. Muller, C. Riekel, 2002 Elsevier Science Ltd., Carbon 40 (2002) pp. 2727-2735.

Notification of Transmittal of the International Search Report and the Written Opinion of the International Searching Authority or the Declaration, Dated May 26, 2006.

A. Bergmann, D. Orthaber, G. Scherf, O. Glatter, "*Improvement of SAXS measurements on Kratky slit systems by Göbel mirrors and imaging-plate detectors*", Journal of Applied Crystallography, (2000), 33, pp. 869-875.

European Office Action for Serial No. 06 717 483. 9-2204, Dated Apr. 23, 2008.

2D beam shaping x Ray optics, http://www.xenocs/products/2d-beam-shaping-x-ray-optics.html, dated Jun. 29, 2011.

Benjamin Chu, Paul J. Harney, Yingjie Li, Kung Linliu, and Fengji Yeh, "A laser-aided prealigned pinhole collimator for synchrotron x rays", Rev. Sci. Instrum. 65 (3), Mar. 1994, 1994 American Institute of Physics, pp. 597-602.

M. Schuster M. Göbel, "Application of Graded Multilayer Optics in X-ray Diffraction", Siemens AG, Advances in X-ray Analysis, vol. 39, 1997, pp. 57-71.

Axo Dresden GmbH, "Applied X-ray Optics and High Precision Deposition", AXO-Prospectus_web.pdf , Mar. 3, 2011, pp. 1-17.

Bob B. He, Uwe Preckwinkel, and Kingsley L. Smith, "Comparison Between Conventional and Two-Dimensional XRD", JCPDS—International Centre for Diffraction Data, Advances in X-ray Analysis, vol. 46, 2003, pp. 37-42.

Licai Jiang, Zaid Al-Mosheky, and Nick Grupido, "Basic principle and performance characteristics of multilayer beam conditioning optics", Powder Diffraction, vol. 17, No. 2, Jun. 2002, pp. 81-93.

Carsten Michaelsen, "Workshop W11: Multilayer X-ray Optics" Innovative Coating Technologies, 2005, pp. 1-43.

Baoping Bob He, Uwe Preckwinkel and Kingsley L. Smith, "Fundamentals of Two-Dimensional X-ray Diffraction (XRD2)", JCPDS—International Centre for Diffraction Data, Advances in Xray Analysis, vol. 43, 2000, pp. 273-280.

X-ray Optics for 2-dimensional beam shaping, http://www.incoatec.de/products/montel-optics, dated Jun. 29, 2011.

O. Glatter and O. Kratky, "Small Angle X-ray Scattering", 1982, pp. 53-103.

Severin Seifert, Juergen Neubauer, Friedlinde Coetz-Neunhoeffer, and Hubert Motzet, "Application of 2-dimensional XRD for the Characterization of Microstructure of Self-Leveling Compounds (SLC)", Feb. 2008, p. 1.

Benjamin Chu and Benjamin S. Hsiao, "Small-Angle X-ray Scattering of Polymers", American Chemical Society, Chemical Reviews, Vol. 101, No. 6, 2001, pgs. 1727-1761.

R. Dietsch and Th. Holz, "High Presision Deposition and Multilayer X-ray Optics", Jul. 2008, p. 1.

Toelher, "X-ray Optics Considerations for Enhancing Beamline Performance", Jul. 2008.

Bob B. He and Uwe Preckwinkel, "X-ray Optics for Two-Dimensional Diffraction", JCPDS—International Centre for Diffraction Data, Advances in X-ray Analysis, vol. 45, 2002, pp. 332-337.

Osamu Yoda, "A New High-Resolution Small-Angle X-ray Scattering Apparatus Using a Fine-Focus Rotating Anode, Point-Focusing Collimation and a Position-Sensitive Proportional Counter", J. Appl. Cryst., vol. 17, 1984, pp. 337-343.

* cited by examiner

TWO DIMENSIONAL SMALL ANGLE X-RAY SCATTERING CAMERA

CROSS-REFERENCE TO RELATED APPLICATIONS

This application is a continuation of U.S. Ser. No. 11/948,304, filed Nov. 30, 2007, which is a continuation of Patent Cooperation Treaty Application No. PCT/US2006/000290 filed Jan. 4, 2006, which is a continuation of and claims priority to U.S. Ser. No. 11/142,862 filed May 31, 2005, now U.S. Pat. No. 7,139,366 B1 issued Nov. 21, 2006, entitled "Two-Dimensional Small Angle X-Ray Scattering Camera," all of which are incorporated herein by reference.

BACKGROUND

The present invention relates generally to an x-ray scattering camera, and more particularly relates to a two-dimensional x-ray scattering camera.

In x-ray scattering, the performance of the camera is typically characterized by the flux, the resolution, defined as the beam diameter at the detector position divided by the sample-to-detector distance, and a parameter $Q_{min}$, defined as $$Q_{min} = \frac{4\pi}{\lambda} \sin\theta_{min},$$

where $\lambda$ is the wavelength and $\theta_{min}$ is the minimum access angle (i.e., the smallest angle, relative to the primary beam, at which meaningful scattering can be collected). In general, increasing the resolution of the system decreases the flux and $Q_{min}$, whereas increasing the flux decreases the resolution and $Q_{min}$.

To address these issues, a camera known as a Kratky camera using a collimation block and an x-ray source in a line projection was developed. The Kratky camera has achieved high resolution, good flux and $Q_{min}$, but it is a one-dimensional camera and therefore suffers from smearing. Although many de-smearing procedures have been developed, some amount of information is still unavoidably lost. Moreover, because of its one-dimensional nature, the Kratky camera can be used only for isotropic samples. The pinhole camera, such as three-pinhole systems, were developed to overcome some of the shortcomings of the Kratky camera. The pinhole camera eliminates the lateral smearing caused by a one-dimensional beam, and can be used to investigate anisotropic samples. However, the pinhole camera has a low flux, low resolution, and its $Q_{min}$ is limited to about 0.005 Å$^{-1}$. In sum, the fundamental limitations of each type of camera have not been overcome: the Kratky camera cannot be used for investigating anisotropic samples, and the pinhole camera cannot achieve a very high resolution and low $Q_{min}$.

From the above, it is seen that there exists a need for an improved two-dimensional camera with high resolution and low $Q_{min}$.

BRIEF SUMMARY

A two-dimensional x-ray scattering camera includes a source, an optic, a detector, and a pair of collimating blocks. The source emits x-ray beams that are reflected by the optic towards a sample. The detector detects scattering from the sample, the pair of collimating blocks is positioned between the optic and the detector to collimate the beam. The bottom surface of one block is substantially parallel to the top surface of the other block, and the blocks are rotatable relative to the beam about a pivot.

A particular feature of this system is that the beam intensity distribution at the detector position is independent of the block collimation, which by nature is asymmetric. Such a beam can be formed by using a two-dimensional multilayer optic (μCMF) and a microfocusing source. The combination of these two elements (block collimation and the highly defined two-dimensional beam) offers a camera with a low $Q_{min}$ and high resolution.

Some embodiments of the invention may have one or more of the following advantages. The camera can be used to investigate anisotropic material and can be configured into a high resolution reflectometer, or a high resolution reflective SAXS camera. Since the sample-to-detector distance is not necessarily as long as in the pinhole camera case, the camera has a large angular range and may make it possible to use the camera in wide angle scattering.

Further advantages and features of the invention will become apparent from the following detailed description and from the claims.

BRIEF DESCRIPTION OF THE DRAWINGS

The accompanying drawings, incorporated in and forming a part of the specification, illustrate several aspects of the present invention and, together with the description, serve to explain the principles of the invention. The components in the figures are not necessarily to scale, emphasis instead being placed upon illustrating the principles of the invention. Moreover, in the figures, like reference numerals designate corresponding parts throughout the views. In the drawings.

DETAILED DESCRIPTION

Figure 1:
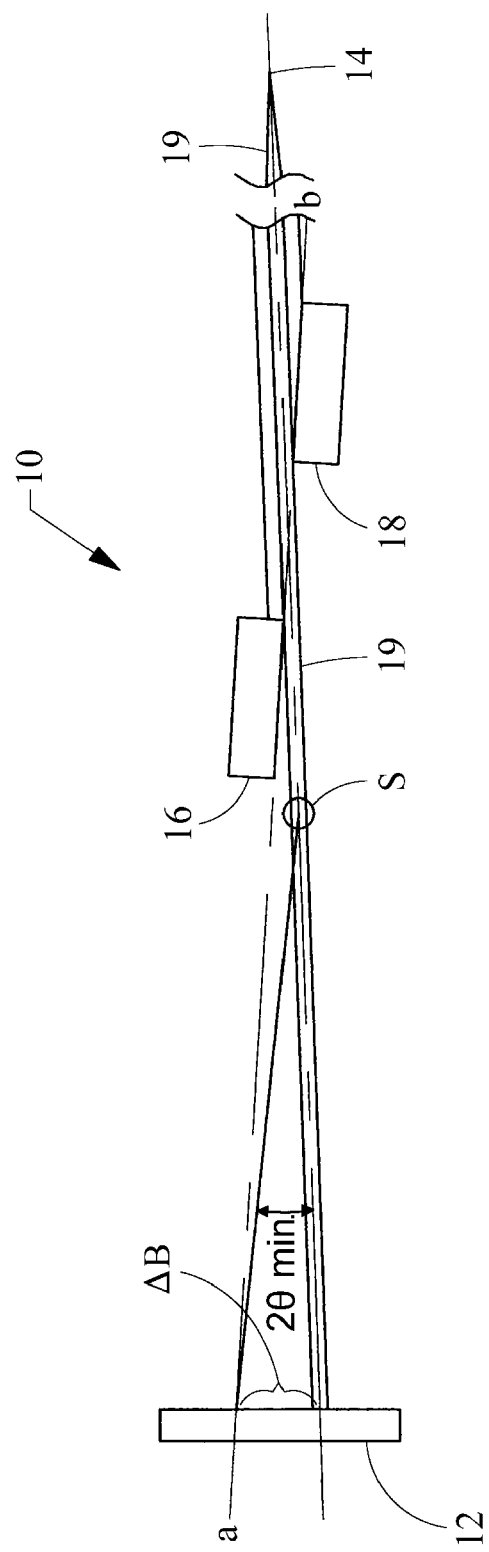
FIG. 1 is a schematic illustration of a Kratky camera.

FIG. 1 depicts a Kratky camera 10 commonly used for small angle x-ray scattering. The camera 10 includes a detector 12 and an x-ray source 14. The x-ray source 14 is a one dimensional line source. X-rays are collimated by a pair of blocks 16 and 18 aligned in a common plane (i.e. the plane of the paper). The collimation blocks direct x-rays 19 at a sample (S), the scattering of which is captured by the detector 12. When the two blocks 16 and 18 are properly aligned, there is no parasitic scattering beyond the line extending between the points a-b.

A Ni filter can be employed to suppress Kβ radiation and soft continuous x-rays. The Kratky camera 10 has good flux and $Q_{min}$ but the one-dimensional nature of the Kratky camera 10 makes it suitable for use with only isotropic samples. Moreover, the Kratky camera produces a scattered x-ray pattern that suffers from severe distortion know as smearing. Although many de-smearing routines have been proposed and implemented, some information is unavoidably lost, and therefore, the resolution, in particular, $\Delta d/d$, where $\Delta d$ is the smallest resolvable d-spacing at the specific d, is compromised.

Recently, Kratky cameras have employed focusing multilayer optics that enhances the performance of the camera. For example, the flux can be increased by a factor of about forty with the use of multilayer optics. Moreover, the background noise caused by K$\beta$ and Bremsstrahlung radiation is removed, and the resolution, which can be measured by the beam width at the detector ($\Delta B$) divided by the distance between the sample and the detector (SD), is improved because of the enhanced focusing capabilities of the optics. Nonetheless, the one-dimensional nature and the smearing problems associated with the Kratky camera remain.

Figure 2:
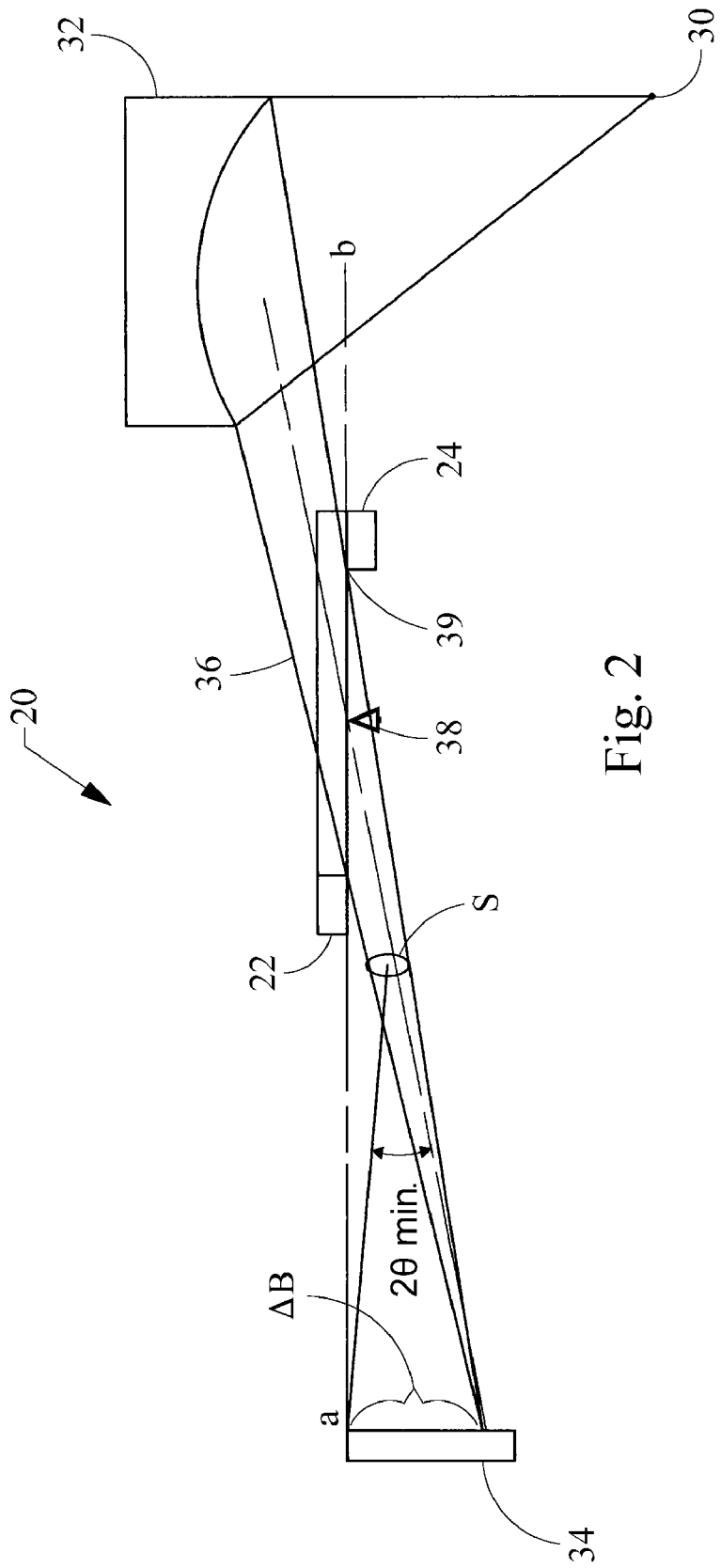
FIG. 2 is a schematic illustration of a camera with a two-dimensional x-ray source in accordance with the invention.
Figure 3:
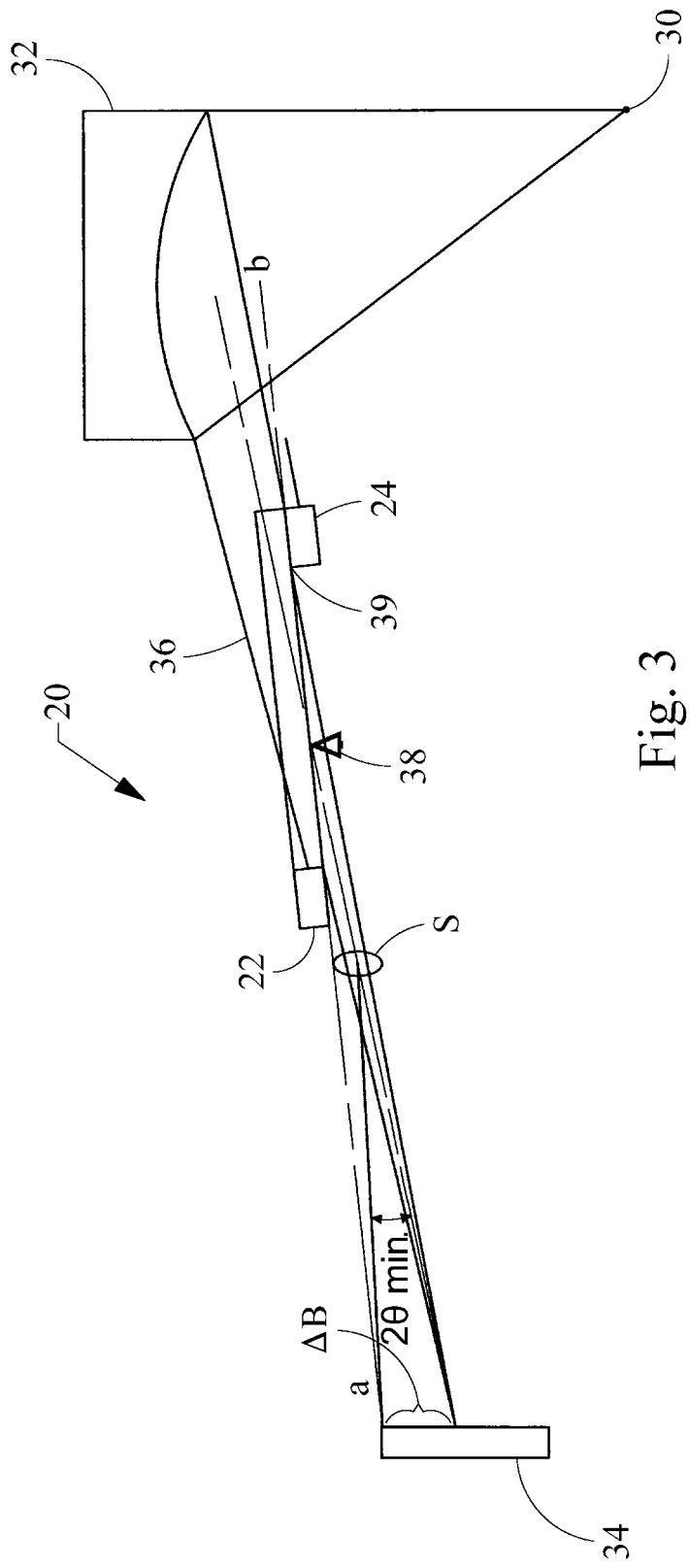
FIG. 3 is a schematic illustration of the collimation blocks rotated about a pivot to adjust the camera's resolution and $Q_{min}$.
Figure 4:
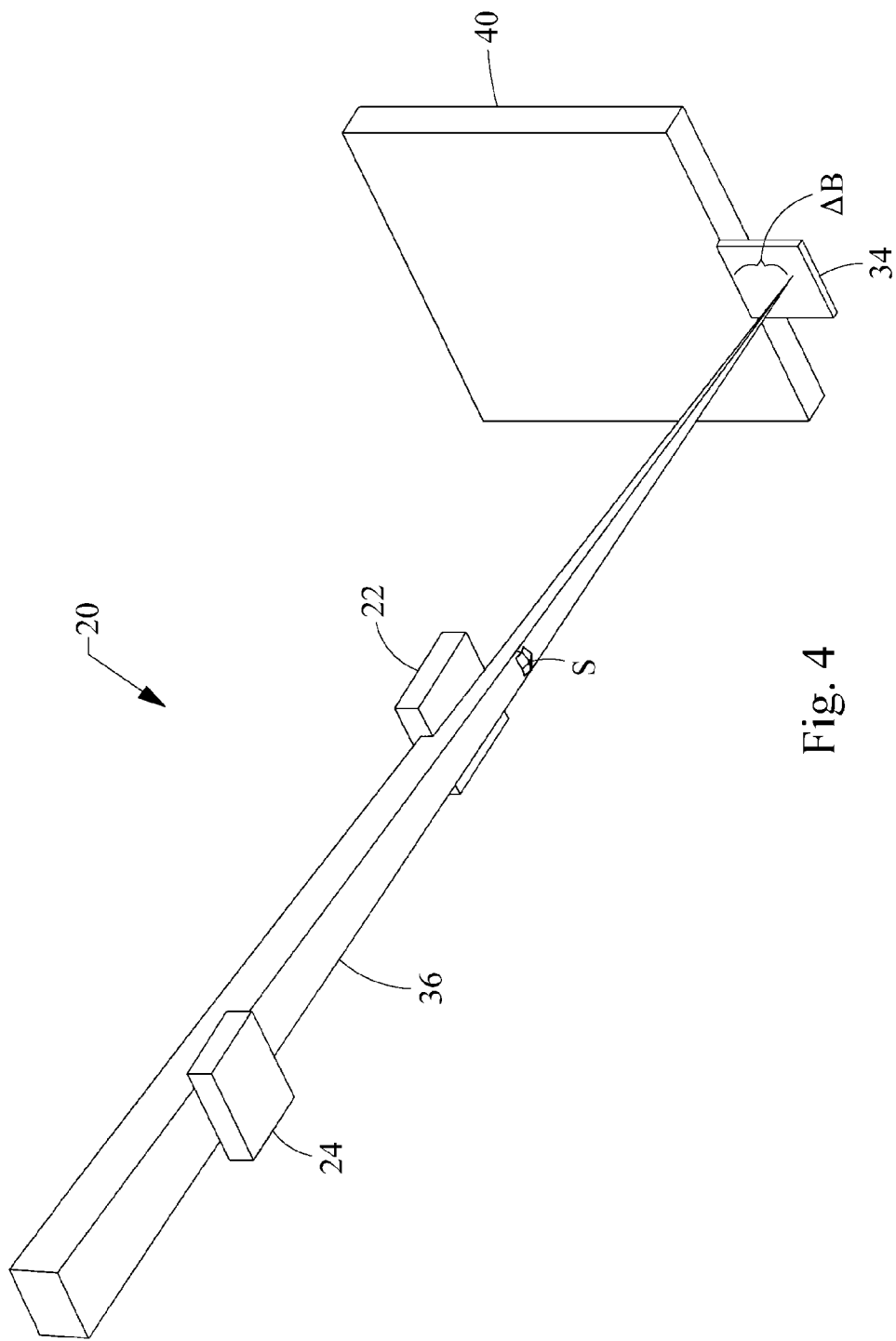
FIG. 4 is a perspective view of a portion of the camera shown in FIGS. 2 and 3.

Referring now to FIGS. 2, 3, and 4, a two-dimensional camera 20 includes a pair of collimating blocks 22 and 24, a microfocusing source 30 and an optic 32, such as a two-dimensional multi-layer optic (or μCMF optic) in accordance with the invention. The optic 32 can be of the type described in U.S. Pat. No. 6,041,099 or U.S. Pat. No. 6,014,423, the entire contents of which are incorporated herein by reference. The combination of the microfocusing source 30 and the optic 32 produces a well defined two-dimensional beam 36. The two-dimensional beam 36 with the collimating blocks 22 and 24 provides a camera with high resolution and low $Q_{min}$. The camera 20 has exceptional resolution (i.e. good $\Delta d/d$) and angular range ($Q_{min}$ from 0.0003 Å$^{-1}$ to wide angles). The flux from the camera 20 is higher than a system with a rotating anode generator and a CMF optic for the same $Q_{min}$. The $Q_{min}$-range can be easily and continuously changed by rotating the collimating blocks 22 and 24 about, for example, a pivot 38, and moving a beam stop 34 positioned below a detector 40 (FIG. 4) away and towards the detector. Note that in some implementations, the rotation of the collimating blocks 22 and 24 can be about another position, such as edge 39 of the block 24. Note also that the beam stop 34 and detector 40 do not have to rotate with the collimating blocks 22 and 24. Because of the small angular variations, the position of the detector 40 can be fixed without any repositioning, and the position of the beam stop 34 is adjusted to block parasitic scattering or to allow access to a smaller angular zone.

The collimating blocks 22 and 24 offer a parasitic-scattering-free zone above the a-b line identified in FIGS. 2 and 3. Since the beam 36 is well defined and symmetric about the primary beam direction, the scattering pattern is two-dimensional in nature. The beam is symmetric because the deviation of the beam from being focused is determined by the source intensity distribution, which can be considered as symmetric about the primary beam axis. If the beam 36 is a focusing beam and the detector 40 is at the focal point of the optic 40, a high resolution (i.e., small $\Delta B/SD$) can be achieved. Since the spot size of the beam 36 at the detector 40 is mainly determined by the deviation from the ideal focusing, which is in turn caused by the non-point like source, the beam shape at the location of the detector 40 is not affected by the position of the collimating blocks 22 and 24. In other words, the beam shape at the detector 40 does not depend on the setting of a desired $Q_{min}$. The beam 36 at the location of the sample S can be sliced into a rectangular shape, while the shape of the beam as projected onto the plane of the detector 40 remains round. This assures that the scattering pattern is free of distortion from the collimation. Although a "half field" view is adequate for measurements of isotropic samples, for an anisotropic sample, a mechanism may be used to rotate the sample S to acquire data over the 360° field of view.

For example, to study an anisotropic sample, the sample S can be mounted to a stage integrated with the camera 20 so that the stage rotates the sample S about the longitudinal axis of the primary beam 36, enabling the investigator to obtain a complete scattering pattern. The flux of the camera 20 is at least a few times higher, and hence the total integration time is lower, than that of a pinhole camera.

As illustrated in FIG. 3, the $Q_{min}$ can be easily adjusted by rocking the collimating system of blocks 22 and 24 about the pivot 38 at the center of the collimating system. As mentioned above, the rotational center can also be at a corner of one of the collimating blocks. Unlike in a three pinhole system, the beam stopper 34 can also be adjusted by moving it relative to the detector 34.

In contrast to a pinhole camera, the camera 20 provides a much lower $Q_{min}$ range. The $Q_{min}$ can easily reach about 0.0003 Å$^{-1}$, equivalent to a $d_{max}$ (i.e. the maximum resolvable d-spacing) of about 2000 Å angstroms. In contrast, the pinhole camera can achieve a $d_{max}$ of about 1000 with an acceptable flux, which is a distinct disadvantaged compared to the camera 20. In addition, unlike the Kratky camera, the flux of the camera 20 does not decrease as $1/r^2$, where r is the distance between the source and detector. Therefore, the effective length of the camera 20 can be longer than that of the traditional Kratky camera. This longer length improves both the $Q_{min}$ and the resolution $\Delta B/SD$.

Among other advantages, the camera system 20 is very flexible and easy to use. A small detector can be positioned in front of the beam stop 34 (the sample side) to measure the intensity of the primary beam and the absorption of the sample. The angular range can be extended easily for wide angle scattering. Moreover, $\Delta d/d$ is proportional to $\Delta B/SD$, and the small size of a microfocusing source offers superior resolution. In addition, the spot size of the microfocusing source, such as a Bede Scientific's MicroSource™, a company in the United Kingdom, can be adjusted to improve the resolution further.

The camera 20 is quite appropriate for use in medical small angle x-ray scattering, allowing the observation of first order peaks around 900 Å. With parallel beam optics, the camera 20 is quite suitable for use as a reflectometer. The camera 20 can be used in reflective small angle x-ray scattering in surface analysis, such as performed, for example, in semiconductor metrology.

Figure 5:
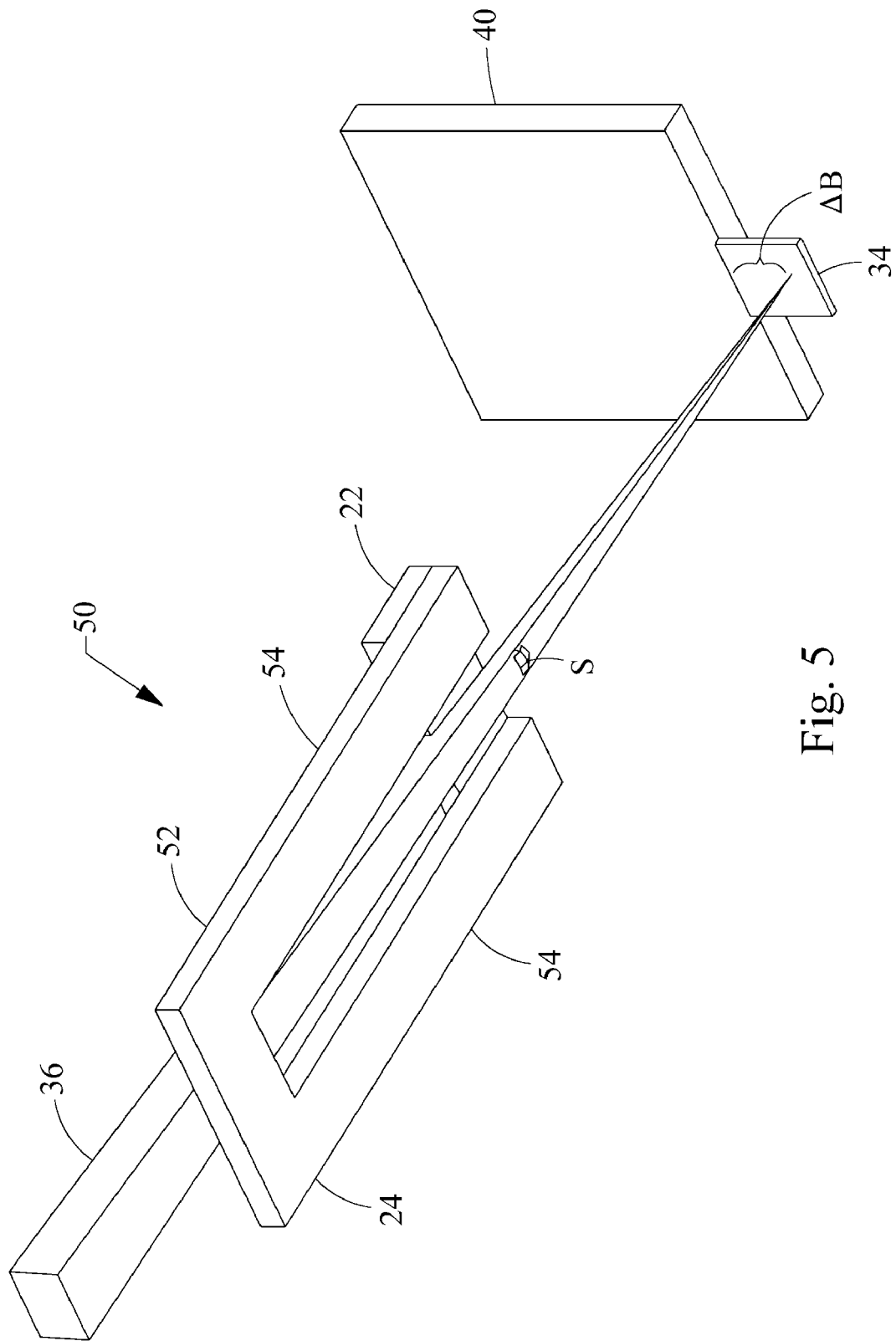
FIG. 5 is an alternative embodiment of a camera with a two-dimensional x-ray source in accordance with the invention.

The blocks 22 and 24 may be integrated as a single unit. For example, an implementation of a two-dimensional camera 50 shown in FIG. 5 includes a U-shaped structure 52 with a top portion that functions as one of the collimating blocks 24. The other collimating block 22 is mounted to the top of the legs 54 of the structure 52 so that the two blocks 22 and 24 are naturally aligned. Alternatively, the block 22 can be a portion of a U-shaped structure, and the block 24 is mounted to it.

Other embodiments are within the scope of the following claims. For example, the beam can be conditioned by forming a two-dimensional beam, enhancing flux and decreasing divergence by collimating or focusing the beam, or monochromatizing the beam to improve its spectrum, or any combination of the foregoing.

What is claimed is:

1. A two-dimensional x-ray scattering camera for analyzing a sample comprising:
   a source which emits x-rays;
   a two-dimensional optic which reflects the x-rays in two dimensions to form a beam of x-rays and directs the beam to interact with the sample;
   a detector which detects x-ray radiation that is scattered by the sample in a parasitic-scattering free zone; and a pair of collimating blocks positioned between the optic and the detector to collimate the beam, a first surface of one block being aligned with a second surface of the other block to form the parasitic-scattering-free zone.

2. The camera of claim 1, wherein angular range of the camera may be adjusted by positioning the pair of collimating blocks.

3. The camera of claim 2, wherein a pivot is located between the pair of collimating blocks, the blocks being rotatable relative to the beam about the pivot.

4. The camera of claim 2, wherein a pivot is located at an edge of one of the collimating blocks, the blocks being rotatable relative to the beam about the pivot.

5. The camera of claim 1, wherein the optic is located between the collimating blocks and the source.

6. The camera of claim 1, wherein the blocks are two separate structures.

7. The camera of claim 1, wherein the blocks are a single integrated unit.

8. The camera of claim 1, further comprising a beam stop, the beam being focused at the detector.

9. The camera of claim 1, wherein the optic is configured to form a two-dimensional beam thereby enhancing flux and decreasing divergence.

10. The camera of claim 1, wherein the optic is configured to collimate the beam.

11. The camera of claim 1, wherein the optic is configured to focus the beam.

12. The camera of claim 1, wherein the optic is configured to monochromatize the beam.

13. The system according to claim 1, wherein one block of the pair of collimating blocks is formed by a U-shaped structure.

14. The system according to claim 13, wherein the other block of the pair of collimating blocks is mounted to the U-shaped structure.

15. The system according to claim 1, wherein the parasitic-scattering-free zone is formed above a line that extends along the first and second surface.

16. The system according to claim 1, wherein the first surface of the one block is aligned in a plane with the second surface of the other block.

17. A method of analyzing a sample with a two-dimensional x-ray beam comprising:
  emitting x-rays from a source;
  reflecting the x-rays from the source to the sample in two-dimensions to form a beam of x-rays;
  collimating the beam with a pair of collimating blocks positioned between the source and the detector, a first surface of one block being aligned with a second surface of the other block to form a parasitic-scattering-free zone; and
  detecting x-ray radiation scattered by the sample with a detector in the parasitic-scattering free zone.

18. The method of claim 17, further comprising forming a two dimensional x-ray beam thereby enhancing flux and decreasing divergence.

19. The method of claim 17, further comprising collimating the beam.

20. The method of claim 17, further comprising monochromatizing the beam.

21. The method of claim 17, further comprising locating the pivot between the pair of collimating blocks.

22. The method of claim 17, further comprising locating the pivot at an edge of one of the collimating blocks.

23. The method of claim 17, further comprising locating the optic between the collimating blocks and the source.

24. The method of claim 17, further comprising focusing the beam at the detector.

25. The method of claim 17, rotating the sample about the longitudinal axis of the beam while collecting a full range of data where the sample is an anisotropic sample.

26. The camera of claim 1, further comprising a rotating device, wherein sample is mounted on the rotation device so that sample is rotated about the longitudinal axis of the beam for collecting a full range of data for an anisotropic sample.

27. The camera of claim 1, wherein the source is a micro-focusing source.

28. The camera of claim 1, wherein the optic is a two-dimensional multilayer optic.

* * * * *